US 6,542,256 B1
(12) United States Patent
Nemoto

(10) Patent No.: US 6,542,256 B1
(45) Date of Patent: Apr. 1, 2003

(54) MEDICINE ENVELOPE PREPARATION SYSTEM

(75) Inventor: Katsuya Nemoto, Omiya (JP)

(73) Assignee: Saitama Medicom Co., Ltd., Saitama (JP)

( * ) Notice: Subject to any disclaimer, the term of this patent is extended or adjusted under 35 U.S.C. 154(b) by 0 days.

(21) Appl. No.: 09/508,272

(22) PCT Filed: Jul. 8, 1999

(86) PCT No.: PCT/JP99/03684

§ 371 (c)(1),
(2), (4) Date: May 11, 2000

(87) PCT Pub. No.: WO00/02780

PCT Pub. Date: Jan. 20, 2000

(30) Foreign Application Priority Data

Jul. 8, 1998 (JP) .......................................... 10-208699

(51) Int. Cl.[7] ............................................... G06K 15/02
(52) U.S. Cl. ..................................... 358/1.18; 358/1.17
(58) Field of Search ................................. 358/1.1, 1.17, 358/1.18; 400/62, 76; 101/35; 206/534; 383/106

(56) References Cited

U.S. PATENT DOCUMENTS 5,390,796 A * 2/1995 Kerfoot, Jr. ................. 206/534
5,839,836 A * 11/1998 Yuyama et al. ............... 101/35
5,852,971 A   12/1998 Yuyama et al.

FOREIGN PATENT DOCUMENTS

| JP | 3030269 | 8/1996 |
| JP | 9-85857 | 3/1997 |
| JP | 9-169325 | 6/1997 |

* cited by examiner

*Primary Examiner*—Arthur G. Evans
(74) *Attorney, Agent, or Firm*—Baker Botts L.L.P.

(57) ABSTRACT

A medicine envelope preparation system for automatically, quickly preparing medicine envelopes having prints of information about medicines contained in the medicine envelopes in response to the simple operation of inputting information about the medicines shown on a prescription, for example. The system includes a storage device whish stores various information about medicines as electronic data; an input device for inputting signals to extract part of the information; a grouping program for grouping the extracted part of information into groups each for a single medicine envelope according to predetermined grouping parameters; and an envelope printer for printing visual data corresponding to each of the groups of the extracted part of information on a single medicine envelope.

5 Claims, 7 Drawing Sheets

FIG. 2

Medicines for Mr. Taro Sanyo
(Patient ID: A1  Reception No. 0)

This table explains effects and ways of potion of your medicines

Medicom Clinic, Hanako Sanyo   June 30, 1998

Page 1/1

| Name of Medicine | Picture | Effects of Medicine | Morn. | Noon | Even. | Before bedding | | Side Effects, etc. | User's Column |
|---|---|---|---|---|---|---|---|---|---|
| Ulcerlmin granular | | It protects rough mucosa. | 1 | | | | for 7 days | Pains at the stomach are removed soon after the use. But continue the use as instructed. | |
| Selbex granular | | It suppresses secretion of acid in the stomach. | Once a day after breakfast | | | | | | |
| Gaster in powder | | | | | | | | | |
| Tanatril tabloid 10 | | It dilates peripheral blood vessels. | 1 | | | | for 7 days | It might make you sleepy and dizzy. Do not drive a car or engage in a dangerous work like that in a height. If coughing continues during the use, consult the doctor. | |
| | | | Once a day after breakfast | | | | | | |
| Norvasc tabloid | | It dilates coronary blood vessels which supply oxygen and nutrition to the heart. | | | | | for 7 days | It might make you sleepy and dizzy. Be careful when you drive a car or engage in a work in a height | |

FIG. 2 (CONTINUED)

| Fernazox capsule 50 mg | It alleviates pains and inflammation. | | for 2 times | Take it after meal instead of at fasting. If you do not take meals, take the medicine together with milk, for example. |
|---|---|---|---|---|
| Daranaide tabloid 50 mg | It's a medicine of glaucoma | | for 2 times | Have food plenty of potassium like orange juice and bananas. |
| Isodine gargle | Gargling chemical for sterilizing the pharynx and mouth | | | Be careful not to drink. When you use it, dilute its 1 to 2 scale units with water of about 60ml (about 1/3 cup), and gargle several times a day. |

| | 30 | 01 | 02 | 03 | 04 | 05 | 06 | 07 | 08 | 09 | 10 | 11 | 12 | 13 | 14 |
|---|---|---|---|---|---|---|---|---|---|---|---|---|---|---|---|
| Morn. | | | | | | | | | | | | | | | |
| Noon | | | | | | | | | | | | | | | |
| Even. | | | | | | | | | | | | | | | |
| Before bedding | | | | | | | | | | | | | | | |

If you have anything unclear, ask us.

Saitama Medicom Pharmacy

Tel. 048-664-1733

FIG. 3A

Patient ID A1
Reception No. 0

INTERNAL USE

Date of Birth 30/01/12

Mr. Taro Sanyo
Once a day after breakfast for 7 days

| Name of Medicine | Picture | Effects of Medicine | Morning | Noon | Evening | Before Bedding |
|---|---|---|---|---|---|---|
| Ulcerlmin granular |  | It protects rough mucosa. It suppresses secretion of acid in the stomach. | 1 | | | |
| Selbex granular | | | | | | |
| Gaster in powder | | | | | | |
| Tanatril tabloid 10 |  | It dilates peripheral blood vessels. | 1 | | | |
| Norvasc tabloid |  | It dilates coronary blood vessels which supply oxygen and nutrition to the heart. | 1 | | | |

June 30, 1998

Saitama Medicom Pharmacy
1122-1 Bessho-cho, Omiya-shi, Saitama
Tel. 048-664-1733  Facsimile. 048-664-1285

Signature of
Pharmacist

FIG. 3B

|  | | Patient ID | A1 |
|---|---|---|---|
|  | | Reception No. | 0 |

TEMPORARY USE

Date of Birth 30/01/12

Mr. Taro Sanyo

| Name of Medicine | Picture | Effects of Medicine | Way of Potion |
|---|---|---|---|
| Fernazox capsule 50 mg |  | It alleviates pains and inflammation. | Use it when having pains. 2 capsules each time For two times |
| Daranaide tabloid 50 mg |  | It's a medicine of glaucoma | Use it when having pains. One tablet each time. For two times. |

June 30, 1998

Saitama Medicom Pharmacy 1122-1 Bessho-cho, Omiya-shi, Saitama      Signature of Tel. 048-664-1733   Facsimile. 048-664-1285      Pharmacist

|  | Patient ID    A1 |
|  | Reception No.    0 |

EXTERNAL USE

Date of Birth 30/01/12

Mr. Taro Sanyo

| Name of Medicine | Picture | Effects of Medicine | Way of Use |
|---|---|---|---|
| Isodine gargle |  | Gargling chemical for sterilizing the pharynx and mouth | |

June 30, 1998

Saitama Medicom Pharmacy 1122-1 Bessho-cho, Omiya-shi, Saitama

Tel. 048-664-1733   Facsimile. 048-664-1285

Signature of
Pharmacist

| Information about Medicines | | | | | Printing Conditions | | |
|---|---|---|---|---|---|---|---|
| No. | Grouping Parameters | | | | | Page | Color Distinction of type of Medicines |
| | Doctors | Types of Medicines | Duration of Use | Mode of Potion | Names of Medicines | | |
| 1 | Doctor Taro | Internal Use | 10 days | 3 times a day after every meal | A in powder | 1 | Black (internal use) |
| 2 | Doctor Taro | Internal Use | 10 days | 3 times a day after every meal | B in powder | | |
| 3 | Doctor Taro | Internal Use | 10 days | once a day after supper | C in powder | 2 | Black (internal use) |
| 4 | Doctor Taro | Internal Use | 10 days | once a day after supper | D in powder | | |
| 5 | Doctor Taro | Internal Use | 3 days | once a day after supper | D in powder | 3 | Black (internal use) |
| 6 | Doctor Taro | Temporary Use | 3 times | on fever | E in powder | 4 | Yellow-Green (temporary use) |
| 7 | Doctor Taro | External Use | ——— | several times a day | F in Liquid | 5 | Red (external use) |
| 8 | Doctor Jiro | Internal Use | 10 days | 3 times a day after every meal | G in powder | 6 | Black (internal use) |
| 9 | Doctor Jiro | Internal Use | 10 days | 3 times a day after every meal | H in powder | | |

MEDICINE ENVELOPE PREPARATION SYSTEM

TECHNICAL FIELD

This invention relates to a system for fabricating a medicine envelope for containing a medicine given by a hospitals or pharmacy according to a medical prescription, especially having thereon written information about the contained medicine.

BACKGROUND ART

Conventional medicine envelopes containing medicines given by hospitals or pharmacies according to medical prescriptions had very simple information such as types of medicines, and durations of use of the medicines, and ways of medicines, which is written directly on the envelopes or written on seals stuck onto the envelopes. With these envelopes, however, information given to patients about the medicines was insufficient, and there was the possibility of misleading patients to take the medicines erroneously.

As a countermeasure of this problem, Japanese Utility Model Publication No. 3030269 discloses a medicine envelope having a print of names of prescribed medicines, information about their effects, their pictures, time for taking the medicines and their doses.

Since the envelope disclosed in the above publication demonstrates much more information about the contained medicines, the patient can readily understand effects of the medicines and can take the medicines properly without misunderstanding the time and dose of each medicine. Additionally, since information about the medicines is directly printed on the envelope, pharmacists can prepare medicines for individual patients more easily and quickly.

The existing envelope proposed in the above publication, however, has a print of the column for the patient's name, column for instructions about ways of potion of the medicines, column for indicating names and information of the medicines, column for demonstrating pictures of the medicines, and column for indicating the time for taking the medicines and their doses, and required statements are shown in these columns.

Although the above publication does not describe details about ways of printing, its basic concept is to prepare a computerized pattern having various columns, install it into a general-purpose computer (such as personal computer) or a word processor and visually display it, then input necessary statements according to the prescription through the key board or from a storage of the computer, and print the input data onto a surface of an envelope with a printer.

Therefore, an operator has to input pieces of information from the prescription into predetermined columns, individually, while watching the display, and this mode of input operation requires much time and labor.

Especially, for the purpose of preventing misuse of medicines, different medicine envelopes have to be used for different groups of medicines which are classified according to grouping parameters like names of doctors who make the prescriptions, types of medicines (internal use, temporary use, external use), duration of use of medicines, ways of potion, and so forth.

Therefore, the operator has to input information about medicines and others shown on the prescription dividing it into one for an envelope and the other for another envelope. This mode of operation is much complicated and liable to invite errors, and hence needs a later job of confirmation.

It is therefore an object of the invention to provide a system capable of quickly and easily fabricating a medicine envelope with an accurate print of various information about medicines.

DISCLOSURE OF INVENTION

A medicine envelope preparation system according to the invention comprises: a storage device whish stores various information about medicines as electronic data; an input device for inputting signals to extract part of the information; a grouping program for grouping the extracted part of information into groups each for a single medicine envelope according to predetermined grouping parameters; and an envelope printer for printing visual data corresponding to each of the groups of the extracted part of information on a single medicine envelope.

In the medicine envelope preparation system according to the invention, distinction about types of medicines is used as one of the grouping parameters, and the envelope printer may be a color printer which can print all or part of the printed matters on medicine envelopes in different colors such that the color on envelopes for one of the groups be different from the colors on envelopes for the others groups. In this manner, envelopes for different groups can be distinguished more easily, and this contributes to preventing erroneous use of the medicines and at the same time enabling quick and precise preparation of the medicines for individual patients.

The medicine envelope preparation system according to the invention may further comprise an additional printer for printing a sheet of instructions about medicines which are contained in the extracted part of information. In this case, a medicine instruction sheet for giving instructions about medicines contained in a medicine envelope can be printed simultaneously with the printing of the envelope.

BRIEF DESCRIPTION OF DRAWINGS

FIG. 2 is a plan view showing an exemplary medicine sheet which is printed according to the same embodiment shown in FIG. 1;

FIGS. 3A, 3B and 3C show front views of medicine envelopes prepared by the embodiment of the invention shown in FIG. 1; and FIG. 4 is a diagram showing an example of grouping information according to grouping parameters.

BEST MODE FOR CARRYING OUT THE INVENTION

Embodiments of the invention are explained below in detail with reference to the drawings.

Figure 1:
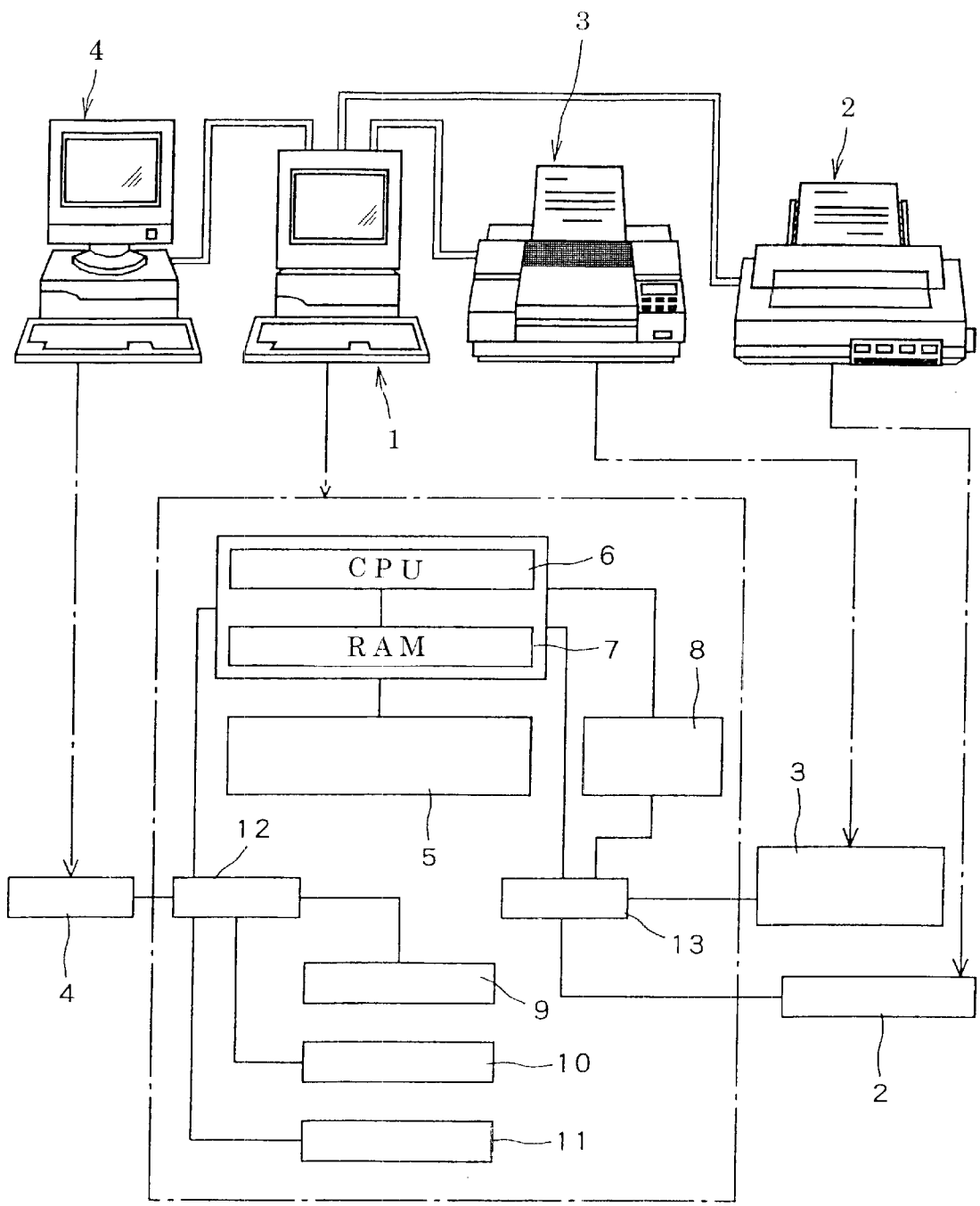
FIG. 1 is a diagram combining a sketch of an embodiment of the invention and a corresponding block circuit diagram.

FIG. 1 shows an envelope preparation system according to a preferred embodiment of the invention. Major components of the system are a general-purpose computer 1, an envelope printer 2 connected to the general-purpose computer 1 and capable of color printing, an instruction sheet printer 3 connected to the computer 1, and a pharmaceutical charge calculating computer as an input device 4 which is connected to the computer 1.

The general-purpose computer 1 has a storage device (fixed magnetic disc) 5 which electronically stores a plurality of units of information each including information about a single medicine together with a color image data of the outer aspect of the medicine. The general-purpose computer 1 further includes a central processing unit (CPU) 6, main storage device (RAM) 7 and grouping program 8. Additionally, connected to an input circuit 12 are a key board 9, disc device 10, image intake device 11 such as digital camera, video camera or scanner, and input device 4, respectively.

Connected to an output circuit 13 of the general-purpose computer 1 are the envelope printer 2 and the instruction sheet printer 3.

To actually use the above-explained medicine envelope preparation system, units of information each including the name of a medicine, effects of the medicine, way of its potion, precautions on the medicine, and so forth, are previously stored together with a color image of the outer aspect of the medicine in the storage device (fixed magnetic disc) 5 in form of an electronic data.

Although such information may be input by using the key board 9, disc device 10 and image intake device 11, it is recommended to use data-base software previously installed in the storage device (fixed magnetic disc) 5. Considering that a large quantity of various kinds of information will be required and most of the information can be commonly used in many hospitals and pharmacies, it will be advantageous to acquire and store such information in the storage device (fixed magnetic disc) 5 from a floppy disc or CD-ROM storing that information through the disc device 10. In this manner, operators will be able to accomplish their operations for preparation of medicine envelopes quickly and easily.

Under the condition, when the name of the doctor, name of the medicine, etc. shown on a prescription are input to a pharmaceutical charge calculating computer (input device) 4 in a pharmacy, for example, selection signals for selecting necessary data corresponding to the input items from the information stored in storage device (fixed magnetic disc) 5 are sent from an output circuit (not shown) of the input device 4 to the input circuit 12.

In response to the selection signals entered into the input circuit 12, the central processing unit (CPU) 6 selects requested data from the information stored in the storage device (fixed disc) 5, and issues corresponding output signals.

Certain part of the output signals from CPU 6 is sent directly to the output circuit 13, and the instruction sheet printer 4 connected to the output circuit 13 prints the selected information, and outputs a pharmaceutical instruction sheet 14 (see FIG. 2).

Figure 3C:

All or part of the output signals from CPU 6 is sent to the output circuit 13 via the grouping program 8 and classified thereby into groups for respective envelopes. Then, these different groups of information are printed by the envelope printer 2 on different envelopes 15, 16, 17 as shown in FIGS. 3A, 3B and 3C, for example.

Next explained is grouping or classification by the grouping program 8 in greater detail.

FIG. 4 shows an example of grouping or classification by the grouping program 8 used in the invention.

At the first step of grouping by the grouping program 8, Data No. 1 through Data No. 9 which are information about medicines and input through the input device 4 on the basis of the prescription made for a certain patient on a day or simultaneously, are sorted by using grouping parameters, i.e. names of doctors, types of medicines, ways of potion and names of medicines.

In this example, this sorting is conducted in the order of names of doctors, types of medicines, ways of potion and names of medicines. However, the sorting order may be modified appropriately.

After that, with reference to FIG. 4, Data No. 1 through Data No. 9 are checked in contents of grouping parameters, and sorted into groups each of an amount that can be printed on one medicine envelope. Individual groups of sorted data are sent as materials to be printed on respective pages to the output circuit 13 shown in FIG. 1, and printed on respective medicine envelopes by the envelope printer 2.

That is, Data No. 1 and Data No. 2 in FIG. 4 are common in contents of all grouping parameters except the names of medicines, and are treated as materials to be printed on a common medicine envelope. In contrast, Data No. 1 is different from Data No. 1 and Data No. 2 in ways of potion as one of the grouping parameters. Therefore, Data No. 3 is output separately from Data No. 1 and Data No. 2 so as to be printed on page 2 under the printing conditions.

In this manner, as a result of grouping of these Data No. 1 through Data No. 9, they are printed on 6 pages, i.e., six medicine envelopes, separately.

In the preferred embodiment of the invention, a color printer is used as the envelope printer 2. Therefore, when printing the classified data on medicine envelopes, different envelopes which are different at least in the portion of statement about types of medicines can be printed with different colors, using black for internal use, yellow-green for temporary use and red for external use, for example, to enable easier distinction of types of medicines with colors.

As explained above, according to the preferred embodiment of the invention, by the easy operation of inputting information about medicines written on a prescription through the input device which also functions as a pharmaceutical charge calculator, it is possible to automatically select necessary part of information about medicines including pictures of outer aspects of the medicines from information stored in the storage device 5, and automatically accomplish not only calculation of pharmaceutical charges but also preparation of instruction sheets about the medicines and necessary medicine envelopes.

Particularly, since medicine envelopes can be printed in different colors at least at the portion of statement of types of medicines to enable distinction with colors, patients can distinguish ways of potion at a glance, and are not misled to erroneous use of the medicines.

Additionally, the use of colors for distinguishing types of medicines, pharmacies can stock medicines by an appropriate mode of distinction among different types of medicines by colors so that their operators can quickly and easily select and bag requested medicines by using the envelopes.

Although the preferred embodiment of the invention has been explained as automatically coloring statements about types of medicines in different colors to enable easy and clear distinction of types of medicines on respective medicine envelopes, any other portion on the envelopes, including lines of tables for information about medicines in FIGS. 3A through 3C, can be printed in different colors for distinction among different envelopes for different types of medicines. It is also possible to color the envelopes themselves in different colors.

Further, the preferred embodiment of the invention has been explained as printing on a common page, i.e. common medicine envelope, all of the information about medicines in a common group, which are common in grouping parameters. However, if the information for a single common group is too much to be printed on a single envelope, part of the information beyond one page may be printed on the next medicine envelope.

As described above, the medicine preparation system according to the invention can automatically and quickly prepare medicine envelopes with various information about medicines by an easy operation of inputting data about medicines and other items shown on a prescription, and operators can efficiently prepare prescribed medicines for patients.

Additionally, by using different colors for printed items among different envelopes distinguished by types of medicines, it is possible to reliably prevent erroneous use of medicines and enable more efficient and quick preparation of medicines for individual patients by using the envelopes with color prints.

Furthermore, when the system is configured to simultaneously prepare sheets representing instructions about medicines, no other device is needed for preparing such sheets, and the system greatly improves the efficiency of operation in pharmacies, and is advantageous from the economical viewpoint as well.

INDUSTRIAL APPLICABILITY

The medicine envelope preparation system according to the invention is useful for quick preparation of envelopes with printed information about medicines contained therein and for improvement of efficiency in preparation of medicines in accordance with prescriptions in hospitals and pharmacies. It enables simultaneous preparation of medicine envelopes and instruction sheets about the medicines, and is suitable for greater efficiency of pharmaceutical operations.

What is claimed is:

1. A medicine envelope preparation system, comprising:

a storage device which stores various information about medicines as electronic data;

an input device for inputting signals to extract part of said information;

a grouping program which uses predetermined grouping parameters to group said extracted part of said information into a plurality of groups which each correspond to a respective one of a plurality of medicine envelopes; and an envelope printer for printing respective visual data on respective said envelopes, said visual data on each said envelope corresponding to a respective said group;

wherein distinction about types of use of medicines is used as one of said grouping parameters, and said envelope printer is a color printer which can print all or part of said visual data for respective said groups on respective said medicine envelopes in respective different colors, such that the color on one of said envelopes for selected said visual data for one of said groups is representative of a first said type of use, and the color on another of said envelopes for selected said visual data for another of said groups is representative of a second said type of use different from said first type of use.

2. The medicine envelope preparation system according to claim 1 further comprising a further printer for printing a sheet of instructions about medicines which are contained in said extracted part of information.

3. The medicine envelope preparation system according to claim 1, wherein said first and second types of use are each one of internal use, external use, and temporary use.

4. The medicine envelope preparation system according to claim 1, wherein said printer respectively uses black, red, and yellow-green for respective envelopes which respectively correspond to internal use, external use, and temporary use.

5. The medicine envelope preparation system according to claim 1, further comprising a further printer for printing a sheet of instructions about medicines which are contained in said extracted part of said information.

\* \* \* \* \*